United States Patent [19]

Dear et al.

[11] 4,014,926
[45] Mar. 29, 1977

[54] FLUORINATED SULFONIC ACIDS AND DERIVATIVES THEREOF

[75] Inventors: Robert Ernest Arthur Dear, Mount Kisco; Eduard Karl Kleiner, New York, both of N.Y.

[73] Assignee: Ciba-Geigy Corporation, Ardsley, N.Y.

[22] Filed: Dec. 19, 1975

[21] Appl. No.: 642,271

[52] U.S. Cl. .................... 260/513 N; 260/294.8 F; 260/429 R; 260/429.9; 260/431; 260/501.15; 260/501.21; 260/503; 260/507 R; 252/526; 252/545; 252/DIG. 11
[51] Int. Cl.² ........................................ C07C 143/08
[58] Field of Search .................... 260/513 N, 513 F

[56] References Cited

UNITED STATES PATENTS

| | | | |
|---|---|---|---|
| 3,235,549 | 2/1966 | Broussalian | 260/513 N |
| 3,544,597 | 12/1970 | Killam | 260/513 N |
| 3,798,265 | 3/1974 | Bartlett | 260/513 F |

*Primary Examiner*—James O. Thomas, Jr.
*Assistant Examiner*—Nicky Chan
*Attorney, Agent, or Firm*—Nestor W. Shust

[57] ABSTRACT

The invention is directed to fluorinated alkylamido sulfonic acids and salts of the formula

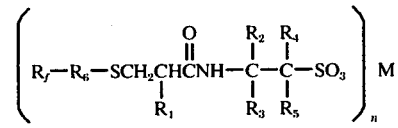

where $R_f$ is straigt or branched chain perfluoroalkyl of 1 to 18 carbon atoms or perfluoroalkyl substituted by perfluoroalkoxy of 2 to 6 carbon atoms, $R_1$ is hydrogen or lower alkyl and each of $R_2$, $R_4$ and $R_5$ is individually hydrogen or a hydrocarbon radical, and $R_6$ is alkylene, alkylenethioalkylene, alkyleneoxyalkylene or alkyleneiminoalkylene with a secondary or tertiary nitrogen atom. $R_3$ is hydrogen, alkyl, aryl or pyridyl, M is hydrogen, a monovalent alkali metal, an alkaline earth metal, an organic base or ammonium, and $n$ is an integer corresponding to the valency of M. Said compounds are prepared by a base catalyzed addition reaction of the thiol, $R_f$-$R_6$SH, to an alkenylamido sulfonic acid salt. The compounds are useful as surfactants and as levelling agents in floor polish formulations.

9 Claims, No Drawings

FLUORINATED SULFONIC ACIDS AND DERIVATIVES THEREOF

DETAILED DISCLOSURE

The present invention is directed to novel fluorinated alkylamido sulfonic acids and salts of the formula

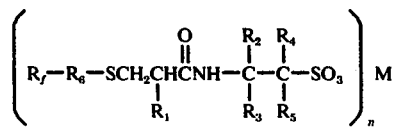

wherein $R_f$ is a straight or branched chain perfluoroalkyl of 1 to 18 carbon atoms or said perfluoroalkyl substituted by perfluoroalkoxy of 2 to 6 carbons.

$R_1$ is hydrogen of lower alkyl, $R_2$, $R_4$ and $R_5$ are independently hydrogen or alkyl group of 1 to 12 carbons, $R_3$ is hydrogen, alkyl of 1 to 12 carbons, phenyl, tolyl or pyridyl, $R_6$ is a straight or branched chain alkylene of 1 to 12 carbons, alkylenethioakylene of 2 to 12 carbons, alkyleneoxyalkylene of 2 to 12 carbon atoms or alkyleneiminoalkylene of 2 to 12 carbon atoms where the nitrogen atom is secondary or tertiary, and M is hydrogen, a monovalent alkali metal, an alkaline earth metal, an organic base or ammonium, and n is an integer corresponding to the valency of M, i.e., 1 or 2.

The alkyl groups of $R_2$, $R_4$ and $R_5$ can be branched or straight chain alkyl of 1 to 18 carbons or cycloalkyl of 3 to 8 carbons. Illustrative examples of such groups are methyl, ethyl, propyl, isopropyl, n-butyl, tert-butyl, n-amyl, tert-amyl, and the various isomers of octyl, decyl and dodecyl, but methyl is preferred. Most preferably $R_4$ and $R_5$ are hydrogen and $R_2$ is methyl.

The group $R_3$ is preferably alkyl and most preferably methyl.

The group $R_1$ is hydrogen or lower alkyl having 1 to 4 carbons, and preferably hydrogen or methyl, and most preferably hydrogen.

The fluorinated alkylamido sulfonic acids and their salts of this invention can be made by the base catalyzed addition reaction of a thiol, $R_f$—$R_6$SH, to an alkenylamidosulfonic acid salt of the formula

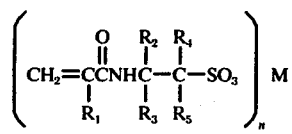

where M is a monovalent alkali metal, an alkaline earth metal, a common organic base or ammonium. The alkali metals particularly useful are sodium, potassium and lithium. M can also be an alkaline earth metal, especially magnesium, calcium, barium, zinc, cadmium or mercury. M can also be derived from organic bases such as trialkylaryl ammonium hydroxides such as benzyl trimethylammonium hydroxide or tetraethylammonium hydroxide, tertiary amines

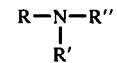

where the R groups are lower alkyls, metal alkoxides, such as sodium methoxide or potassium t-butoxide, aryl or alkyl lithiums such as phenyl lithium, butyl lithium in nonreactive solvents such as tetrahydrofuran, alkali metal amides such as lithium amide or sodium amide and the like. Preferably M is an alkali metal or ammonium, and n is an integer corresponding to the valency of M.

The perfluoroalkyl thiols employed in the preparation of the compounds of this invention are well known in the prior art. For example, thiols of the formula $R_fR_6$—SH have been described in a number of U.S. patents including U.S. Pat. Nos. 2,894,991; 2,961,470; 2,965,677; 3,088,849; 3,172,190; 3,544,663 and 3,655,732.

Thus, U.S. Pat. No. 3,655,732 discloses mercaptans of formula

where $R_6$ is alkylene of 1 to 16 carbon atoms and $R_f$ is perfluoroalkyl and teaches that halides of formula $R_f$—$R_6$—hal are well known; reaction of $R_fI$ with ethylene under freeradical conditions gives $R_f(CH_2CH_2)_nI$ while reaction of $R_fCH_2$ I with ethylene gives $R_fCH_2(CH_2CH_2)_nI$ as is further taught in U.S. Pat. Nos. 3,088,849; 3,145,222; 2,965,659 and 2,972,638.

U.S. Pat. No. 3,544,663 teaches that the mercaptan

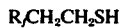

where $R_f$ is perfluoroalkyl of 5 to 13 carbon atoms, can be prepared by reacting the perfluoroalkyl alkylene iodide with thiourea or by adding $H_2S$ to a perfluoroalkyl substituted ethylene ($R_f$—CH=$CH_2$), which in turn can be prepared by dehydrohalogenation of the halide $R_f$—$CH_2CH_2$—hal.

The reaction of the iodide $R_f$—$R_6$—I with thiourea followed by hydrolysis to obtain the mercaptan $R_f$—$R_6$—SH is the preferred synthetic route. The reaction is applicable to both linear and branched chain iodides. Many useful perfluoroalkoxyalkyl iodides are described in Australian Pat. No. 36,868 filed Apr. 24, 1968 of general formula

where m is 1–3.

U.S. Pat. No. 3,655,732 further discloses compounds of formula

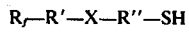

where

R' and R'' are alkylene of 1 to 16 carbon atoms, with the sum of the carbon atoms of R' and R'' being no greater than 25; $R_f$ is perfluoroalkyl of 4 through 14 carbon atoms and X is —S— or —NR'''— where R''' is hydrogen or alkyl of 1 through 4 carbon atoms.

Particularly preferred herein are the thiols of formula $R_fCH_2CH_2SH$ where $R_f$ is perfluoroalkyl of 4 to 12 carbon atoms. These $R_f$-thiols can be prepared from $R_fCH_2CH_2I$ and thiourea in very high yield.

Illustrative examples of preferred perfluoroalkylalkylenethiols are $C_4F_9CH_2CH_2SH$ $C_6F_{13}CH_2CH_2SH$ $C_8F_{17}CH_2CH_2SH$ $C_{10}F_{21}CH_2CH_2SH$ $C_{12}F_{25}CH_2CH_2SH$

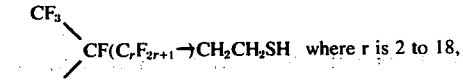

as for example $C_5F_{11}$, $C_7F_{15}$, $C_9F_{19}$, $C_{11}F_{23}$, etc.

Especially preferred perfluoroalkyalkylenethiols are $C_6F_{13}CH_2CH_2SH$ $C_8F_{17}CH_2CH_2SH$ $C_{10}F_{21}CH_2CH_2SH$ and mixtures thereof.

Alkenylamido sulfonic acids and their salts are well known in the art and have been thoroughly described, for example, in U.S. Pat. Nos. 2,983,712; 3,332,904; 3,506,707 and British Pat. No. 1,090,779; and German Offenlegungsschift No. 2,105,030. Illustrative examples are listed below.

2-Acrylamidopropanesulfonic acid
2-Acrylamido-2-methylpropanesulfonic acid
2-Methacrylamido-2-methylpropanesulfonic acid
2-Acrylamidobutanesulfonic acid
3-Acrylamidobutane-2-sulfonic acid
3-Acrylamido-2,3-dimethylbutane-2-sulfonic acid
2-Acrylamido-2,4,4-trimethylpentanesulfonic acid
2-Acrylamido-2-phenylethanesulfonic acid
2-Acrylamido-2-phenylpropanesulfonic acid
2-Acrylamido-2-tolylethane sulfonic acid
2-Acrylamido-2-pyridylethane sulfonic acid Especially preferred is 2-acrylamido-2-methylpropanesulfonic acid, available, commercially from the Lubrizol Corporation. Using preferred reactants, one mole of 2-acrylamido-2-methylpropanesulfonic acid is reacted with one equivalent of a base such as a carbonate as, for example, sodium carbonate, to give an intermediate sodium acrylamido sulfonic acid salt. After carbon dioxide evolution has ceased a perfluoroalkyl thiol such as 1,1,2,2-tetrahydroperfluorooctane thiol, dissolved in a solvent such as methanol, is introduced into the reaction mixture. The second step is carried out in the presence of a catalytic amount of a base, such as sodium hydroxide, to yield the product.

The bases used in Steps 1 and 2 may be the same or they may be different. This has no effect on the course of the reaction, but it is generally more convenient and economical to use bases such that M is the same in both steps. Organic bases are generally used when it is desired to obtain a product with increased solubility over those where M is an alkali metal.

The reactions discussed above would normally be carried out in a solvent to facilitate the reaction.

Useful solvents for the reaction are those which will dissolve significant amounts of the alkenylamidosulfonic salt and of the mercaptan. Typical of these are the more polar solvents such as water, methanol, ethanol, isopropanol and dimethylformamide. Other useful solvents are alcohols such as n-propanol, n- and isobutanol, butyl carbitol, ethylene glycol, propylene glycol 1,2 and 1,3, butylene glycol 1,3 and 1,4 2-methyl-2,4-pentanediol, 2,2-diethyl-1,3-propanediol 1,4-cyclohexanedimethanol (cis and trans) and the like; ethers such as glycol ethers (Dowanols, Carbitols and Cellosolves), ethylene glycol monomethyl ether, ethylene glycol dimethyl ether, ethylene glycol monoethyl ether, ethylene glycol monobutyl ether, diethylene glycol, triethylene glycol, tetraethylene glycol, diethylene glycol monomethyl ether, diethylene glycol monoethyl ether, diethylene glycol diethyl ether, diethylene glycol monobutyl ether, tetrahydrofuran and the like; ketones such as acetone, methyl ethyl ketone, methyl n-propyl ketone, chloroacetone, diacetyl, acetyl acetone, mesityl oxide and the like; N-methyl pyrrolidone, acetonitrile, dioxane and the like.

Step 1 of the reaction is normally carried out at 0° to 25°, although higher or lower temperatures may be employed. Preferably the temperature is controlled at 5°-10° C. This is a simple acid/base neutralization and is thus rapid even at ambient temperatures. Temperatures above about 30° are not recommended since under these circumstances polymerization of the unsaturated amidosulfonic acid may occur. Use of inert gas to blanket the reaction is also useful to prevent unwanted side reactions.

At least a molar equivalent of base is necessary in Step 1 in order that a basic environment will be present in Step 2. Use of an excess of base in Step 1 will not harm the reaction, but large excesses serve no useful purpose and are therefore to be avoided on economic grounds. Step 2 is the base catalyzed addition of a fluorinated mercaptan to the α,β-unsaturated sulfonate formed in Step 1. Step 2 may be carried out at temperatures of 0° to 100°, but to achieve reasonable reaction times, a temperature of 50°-80° is preferred. Under these conditions — e.g., in refluxing methanol or ethanol — reaction is complete in two to two and one half hours. At 25° the reaction is considerably slower.

The compounds of this invention can be converted to the corresponding sulfones and sulfoxides. This can be accomplished by known oixdation methods, such as reacting the thioether with acetic acid and a peroxide, e.g., $H_2O_2$, as described in greater detail in German OS-DT No. 2,334,889 which is incorporated herein by reference.

The examples below are presented for illustrative purposes only and do not limit the scope of the invention. The temperature is expressed in ° C.

EXAMPLE 1

2-Methyl-2-(3-[1,1,2,2-tetrahydroperfluorooctylthio]-propionamide)-1-propanesulfonic acid, sodium salt $C_6F_{13}CH_2CH_2SCH_2CH_2CONHC(CH_3)_2CH_2SO_3Na$ 2-Acycrylamido-2-methylpropanesulfonic acid (10.35 g; 0.05 mole) was placed in a 250 ml three-necked flask fitted with a mechanical stirrer, thermometer, nitrogen inlet and a condenser in the reflux position. Dry methanol (50 ml) was added, followed by sodium carbonate (2.76 g; 0.026 mole) over a 15 minute period. After all $CO_2$ evolution had ceased, 1,1,2,2-tetrahydroperfluorooctane thiol (19.0 g; 0.05 mole), dissolved in a further 50 ml of dry methanol, was added together with 0.04 g (0.0005 mole) sodium hydroxide catalyst. The mixture was stirred 18 hours at 25°, and for 3.5 hours under reflux (65°). At this point all thiol was consumed. The warm product solution was added to 700 ml diethyl ether, cooled to 0° and filtered. The white powdery product was collected and dried at 55°/15 mm Hg overnight, yielding 26.2g (86% yield), M.P. 216°–217°.

EXAMPLE 2

2-Methyl-2-(3-[1,1,2,2-tetrahydroperfluorooctylthio]-promionamide)-1-propanesulfonic acid and potassium salt $C_6F_{13}CH_2CH_2SCH_2CH_2CONHC(CH_3)_2CH_2SO_3K$ Using the apparatus described in Example 1, 2-acrylamido-2-methylpropanesulfonic acid (10.35 g; 0.05 mole) was neutralized in 50 ml methanol with anhydrous potassium carbonate (3.6 g; 0.026 mole). The reaction was continued by the addition of 1,1,2,2-tetrahydroperfluorooctane thiol (19.0 g; 0.05 mole) and potassium hydroxide (0.0005 mole) as a catalyst. Heating the mixture at 65° for two and one half hours completed the reaction. Following the isolation and drying procedures described in Example 1, a total of 29.8 g of a fine white powder was obtained (95.4% of theory). M. P. 221° to 225°.

The free acid was obtained from the above potassium salt in the following manner:

5 g of the salt was dissolved in 100 g deionized water and the solution was passed through a 50 × 1.5 cm column containing 25 g Amberlyst 15 (Rohm & Haas) ion exchange resin. The column was rinsed with a further 100 g of water and the total eluate was evaporated to dryness in a circulative hot air oven at 60°. The solids so obtained were thoroughly dried in a vacuum oven at 55° and 0.1 mm Hg for four hours. The free acid, $C_6F_{13}CH_2CH_2SCH_2CH_2CONHC(CH_3)_2CH_2SO_3H$, was obtained as a hard, brittle wax (4.6 g), which was pulverized to a grey powder.

Elemental Analysis for $C_{15}H_{18}F_{13}O_4S_2N$:
Theoretical: C,30.7; H,3,1;N,2.4; F,42.0.
Found: C,30.5; H,3.2; N,2,5; F,41.3.

EXAMPLES 3 to 7

Following the procedure described in Examples 1 and 2, the following salts, $R_fCH_2CH_2SCH_2CH_2CONHC(CH_3)_2CH_2SO_3M$ were prepared.

| Ex | $R_f$ | M | Yield | Found % C | H | F | N | Required % C | H | F | N |
|---|---|---|---|---|---|---|---|---|---|---|---|
| 3 | $C_8F_{17}$ | Na | 81.8 | 28.42 | 2.48 | 43.36 | 2.14 | 28.79 | 2.41 | 45.53 | 1.97 |
| 4 | $C_8F_{17}$ | K | 89.9 | 28.31 | 2.13 | 44.84 | 1.98 | 23.15 | 2.36 | 44.52 | 1.93 |
| 5 | $C_{10}F_{21}$ | Na | 40.8 | 27.92 | 2.18 | 49.61 | 1.74 | 28.19 | 2.11 | 49.30 | 1.73 |
| 6 | $C_{10}F_{21}$ | K | 23.5 | 27.66 | 2.08 | 49.33 | 1.70 | 27.64 | 2.07 | 48.33 | 1.70 |
| 7 | $R_f$* | Na | 67.6 | | | 44.50 | | | | | |

*$R_f$ in this case is a mixture of $C_6F_{13}$, $C_8F_{17}$ and $C_{10}F_{21}$ in the approximate ratio 1:2:1

In each example the structure of the product was confirmed by nmr examination.

EXAMPLE 8

The surface tensions of dilute aqueous solutions of the anionic surfactants described in earlier examples were determined and compared with FC-95, a commercially available fluorinated anionic surfactant. The table shows that the surfactants of the present invention are more efficient at any given fluorine level than the commercial product, and that useful lowering of aqueous surface tension is obtained at much lower levels of fluorine with the compounds of this invention.

TABLE I

Surface Tension of Anionic Surfactant Solutions

Except where otherwise indicated, all results are reported for 25° ±0.4° C.

$R_fCH_2CH_2SCH_2CH_2CONHC(CH_3)_2CH_2SO_3M$

| Soln of Ex | $R_f$ | M | Surface Tension γs (dynes/cm) at 0.1% F | at 0.05% F | at 0.01% F |
|---|---|---|---|---|---|
| 1 | $C_6F_{13}$ | Na | 26.8 | 23.2 | 29.2 |
| 2 | $C_6F_{13}$ | K | 26.2 | 22.6 | 29.3 |
| 3 | $C_8F_{17}$ | Na | 24.8 | 25.6 | 26.8 |
| 4 | $C_8F_{17}$ | K | 25.0 | 25.8 | 39.4 |
| 7 | $R_f$ | Na | 24.5 | 25.4 | 27.9 |
| FC-95 | | | 28.3/31° C  28.6/29° C Cloudy | 33.3 | 46.6 |

The surfactants of this invention may also be prepared in solution in such a manner that they are suitable for use without isolation of the solid surfactants.

EXAMPLE 9

2-Methyl-2-(3-[1,1,2,2-tetrahydroperfluorooctylthio]-propionamide)-1-propanesulfonic acid, sodium salt $C_6F_{13}CH_2CH_2SCH_2CH_2CONHC(CH_3)_2CH_2SO_3Na$ 2-Acycrylamido-2-methylpropanesulfonic acid (21.74 g; 0.105 mole) was placed in a 250 ml three-necked flask, equipped as described in Example 1. Water (37 g) was added with stirring, then a cooling bath was placed around the flask and, maintaining the temperature at about 10° C, sodium carbonate (5.62 g; 0.053 mole) was added in portions. After all $CO_2$ evolution had ceased, the cooling bath was removed and hexylene glycol (40.2 g) was added as a cosolvent. Sodium hydroxide (0.24 g of 50% solution; 0.003 moles) was added as a catalyst, followed by 1,1,2,2-tetrahydroperfluorooctane thiol (40.28 g; 0.1 mole). The system was stirred for 18 hours at 25° C and at 60° C for further 3 hours. The product was a clear, straw colored viscous liquid consisting of:

45.0% solids: $C_6F_{13}CH_2CH_2SCH_2CH_2CONHC(CH_3)_2CH_2SO_3Na$
26.4% water
28.6% hexylene glycol

EXAMPLE 10

2-Methyl-2-(3-[1,1,2,2-tetrahydroperfluoroalkylthio]-propionamide)-1-propanesulfonic acid, sodium salt $R_fCH_2CH_2SCH_2CH_2CONHC(CH_3)_2CH_2SO_3Na*$ 2-Acrylamido-2-methylpropanesulfonic acid (460.0 g; 2.22 mole) was added to a 5 l flask equipped as described in Example 1. Water (612.4 g) was added and the flask was then placed in a cooling bath while sodium hydroxide (184.8 g of 50% solution; 2.31 mole) was added slowly. During the addition the temperature was controlled to 10° C maximum. The cooling bath was removed and hexylene glycol (744.4 g) and 1,1,2,2-tetrahydroperfluoroalkane thiol (979.9 g; 2.20 moles) was added to the flask, and the resulting slurry was heated to 60° C for 5 hours. GLC examination showed all mercaptan to have been consumed. In this state (50% solids) the product was very viscous, so it was diluted with a further 1276.1 g of water to a readily mobile liquid containing 35% solids.

Composition:
35% solids: $R_fCH_2CH_2SCH_2CH_2CONHC(CH_3)_2CH_2SO_3Na$
47.5% water
17.5% hexylene glycol

* $R_f$ is a mixture of $C_6F_{13}$, $C_8F_{17}$ and $C_{10}F_{21}$ is the approximate ratio 1:1:0.3, with trace amounts of $C_4F_9$ and $C_{12}F_{25}$.

EXAMPLES 11 to 19

Following the procedure of Example 1, the appropriate perfluoroalkyl thiols are reacted with the appropriate alkenylamido-sulfonic acids to yield products wherein the various groups are as shown in Table II below:

TABLE II

| Ex. | $R_f$ | $R_1$ | $R_2$ | $R_3$ | $R_4$ | $R_5$ | $R_6$ | Product |
|---|---|---|---|---|---|---|---|---|
| 11 | $(CF_3)_2CFOCF_2CF_2$ | H | $CH_3$ | $CH_3$ | H | H | $(CH_2)_2$ | $(CF_3)_2CFOCF_2CF_2(CH_2)_2S(CH_2)_2CONHC(CH_3)_2CH_2SO_3M$ |
| 12 | $(CF_3)_2CFCF_2CF_2$ | H | $CH_3$ | $CH_3$ | H | H | $(CH_2)_2$ | $(CF_3)_2CFCF_2CF_2(CH_2)_2S(CH_2)_2CONHC(CH_3)_2CH_2SO_3M$ |
| 13 | $C_8F_{17}$ | H | $CH_3$ | $CH_3$ | $CH_3$ | $CH_3$ | $(CH_2)_2$ | $C_8F_{17}(CH_2)_2S(CH_2)_2CONHC(CH_3)_2C(CH_3)_2SOM$ |
| 14 | $C_6F_{13}$ | $CH_3$ | $CH_3$ | $CH_3$ | H | H | $(CH_2)_2$ | $C_6F_{13}(CH_2)_2SCH_2CH(CH_3)CONHC(CH_3)_2CH_2SO_3M$ |
| 15 | $C_6F_{13}$ | H | $CH_3$ | $CH_2C(CH_3)_3$ | H | H | $(CH_2)_2$ | $C_6F_{13}(CH_2)_2S(CH_2)_2CONHC(CH_3)(CH_2C(CH_3)_3)Cl_2SO_3M$ |
| 16 | $C_8F_{17}$ | H | H | $C_6H_5$ | H | H | $(CH_2)_2$ | $C_8F_{17}(CH_2)_2S(CH_2)_2CONHCH(C_6H_5)CH_2SO_3M$ |
| 17 | $C_8F_{17}$ | H | H | $C_5H_4N$ | H | H | $(CH_2)_2$ | $C_8F_{17}(CH_2)_2S(CH_2)_2CONHCH(C_5H_4N)CH_2SO_3M$ |
| 18 | $C_8F_{17}$ | H | H | $C_6H_4CH_3$ | H | H | $(CH_2)_2$ | $C_8F_{17}(CH_2)_2S(CH_2)_2CONHCH(C_6H_4CH_3)CH_2SO_3M$ |
| 19 | $C_6F_{13}$ | H | $CH_3$ | $CH_3$ | H | H | $(CH_2)_2S(CH_2)_2$ | $C_6F_{13}(CH_2)_2S(CH_2)_2S(CH_2)_2CONHC(CH_3)_2CH_2SO_3M$ |

EXAMPLE 20

This example illustrates the inverse addition of reactants in the first step.

Using the equipment described in Example 1, sodium hydroxide (8.6 g of 50% solution, 0.107 mole) was mixed with 29.6 g deionized water in the reaction flask, and the solution was cooled to 0° C. 2-acrylamido-2-methyl propane sulfonic acid (21.7 g; 0.105 mole) was added slowly, as a powder, at such a rate that the ensuing exothermic reaction maintained the system at 3°–10° C. Total addition required about 30 minutes. The solution was stirred for a further 45 minute period, then 35.88 g hexylene glycol and 1,1,2,2-tetrahydrofluoroalkane thiol (47.5 g; 0.10 mole) were added, and the system was stirred vigorously, under an inert atmosphere, for 5 hours at 60° C. At the end of this time a further 61.1 g deionized water was added to the clear, warm solution to give a product of the following composition:

35% solids: $R_fCH_2CH_2SCH_2CH_2CONHC(CH_3)_2CH_2SO_3Na$
47.5% water
17.5% hexylene glycol $R_f$ is a mixture as previously defined.

EXAMPLE 21

To show the excellent foaming properties of the sulfonate salts, both individually and as mixtures, Ross-Miles foam tests (ASTM D-1173-53) were run at 25° C.

| Compound of Example | Foam Height (mm) | | | |
|---|---|---|---|---|
| | 0.01%* | | 0.1%* | |
| | Initial | 5 Min | Initial | 5 Min |
| 1 | 65 | 55 | 145 | 125 |
| 3 | 110 | 105 | 153 | 138 |
| 2 | 75 | 55 | 170 | 145 |
| 4 | — | — | 45 | 40 |
| 6 | — | — | 15 | 10 |
| 10 | 90 | 85 | 155 | 135 |

EXAMPLE 22

Magnesium bis-2-methyl-2-[3-(1,1,2,2-tetrahydroperfluorooctyl thiol) propionamido]-propanesulfonate $(C_6F_{13}CH_2CH_2SCH_2CH_2CONHC(CH_3)_2CH_2SO_3)_2Mg$ Using the apparatus described in Example 1, magnesium carbonate ($4MgCO_3 \cdot Mg(OH)_2 \cdot nH_2O$; assay 41.5% MgO; 3.65 g, 0.038 mole) was added to 25 ml deionized water in the flask. The system was cooled to 2° and 2-acrylamido2-methyl propane sulfonic acid (15.53 g; 0.075 mole) was added at a rate such that the ensuing exothermic reaction was controlled at about 5°. Good stirring was maintained and the system was placed under a slow stream of nitrogen. 1,1,2,2-tetrahydroperfluorooctane thiol (28.5 g; 0.075 mole) was added followed by 50 g isopropyl alcohol and 2 drops of 50% sodium hydroxide solution as a catalyst. The system then was stirred at 65° for 20 hours and the resulting white emulsion, which was now devoid of mercaptan, was poured into an excess of acetone. The white percipitate which resulted was filtered and dried at 70° and 0.1 mm Hg, to give 41.3 g (91.8% yield) of product.

The structure of the product was confirmed by elemental analysis and n.m.r. spectroscopy.

What is claimed is:

1. A compound of the formula

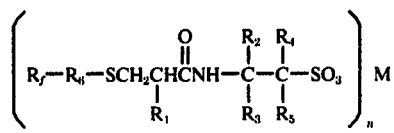

wherein
$R_f$ is a straight or branched chain perfluoroalkyl of 1 to 18 carbon atoms or said perfluoroalkyl substituted by perfluoroalkoxy of 2 to 6 carbons,
$R_1$ is hydrogen or lower alkyl,
$R_2$, $R_4$ and $R_5$ are independently hydrogen or alkyl group of 1 to 12 carbons,
$R_3$ is hydrogen or alkyl of 1 to 12 carbons,
$R_6$ is a straight or branched chain alkylene of 1 to 12 carbons, and
M is hydrogen, a monovalent alkali metal or an alkaline earth metal, and
$n$ is an integer corresponding to the valency of M.

2. A compound of claim 1 wherein $R_1$, $R_4$ and $R_5$ are hydrogen, $R_2$ and $R_3$ are methyl, $R_6$ is straight or branched chain alkylene and M is hydrogen, sodium, potassium, or magnesium.

3. The compound of claim 1 which is 2-methyl-2-(3-[1,1,2,2-tetrahydroperfluorooctylthio]propionamide)-1-propanesulfonic acid, sodium salt.

4. The compound of claim 1 which is 2-methyl-2-(3-[1,1,2,2-tetrahydroperfluorooctylthio]propionamide)-1-propanesulfonic acid, potassium salt.

5. A compound of claim 2 which is in the form of a free acid.

6. Compounds of claim 1 which are a mixture of 2-methyl-2-(3-[1,1,2,2-tetrahydroperfluoroalkylthio]-propionamide)-1-propane-sulfonic acid, sodium salts, wherein the perfluoroalkyl moiety is a mixture of $C_6F_{13}$, $C_8F_{17}$ and $C_{10}F_{21}$.

7. A compound of claim 1 which is a magnesium salt of 2-methyl-2-(3-[1,1,2,2-tetrahydroperfluorooctylthio]propionamide)-1-propanesulfonic acid.

8. A compound of claim 1 which is a sodium, potassium or magnesium salt of 2-methyl-2-(3-[1,1,2,2-tetrahydroperfluorododecylthio]propionamide)-1-propanesulfonic acid.

9. A compound of claim 1 which is a sodium, potassium or magnesium salt of 2-methyl-2-(3-[1,1,2,2-tetrahydroperfluorodecylthio]propionamide)-1-propanesulfonic acid.

* * * * *